(12) United States Patent
Rangnekar

(10) Patent No.: US 7,786,275 B2
(45) Date of Patent: Aug. 31, 2010

(54) IDENTIFICATION OF A UNIQUE CORE DOMAIN OF PAR-4 SUFFICIENT FOR SELECTIVE APOPTOSIS INDUCTION IN CANCER CELLS

(75) Inventor: Vivek M. Rangnekar, Lexington, KY (US)

(73) Assignee: University of Kentucky Research Foundation, Lexington, KY (US)

(*) Notice: Subject to any disclaimer, the term of this patent is extended or adjusted under 35 U.S.C. 154(b) by 797 days.

(21) Appl. No.: 10/726,615

(22) Filed: Dec. 4, 2003

(65) Prior Publication Data

US 2005/0118179 A1 Jun. 2, 2005

Related U.S. Application Data

(60) Provisional application No. 60/430,669, filed on Dec. 4, 2002.

(51) Int. Cl.
*C07K 14/435* (2006.01)
*C12P 21/00* (2006.01)
*C12N 15/00* (2006.01)
*C12N 5/07* (2006.01)

(52) U.S. Cl. .................. 530/388.8; 530/300; 435/69.1; 435/320.1; 435/325; 536/23.1

(58) Field of Classification Search ........................ None
See application file for complete search history.

(56) References Cited

U.S. PATENT DOCUMENTS

2006/0141451 A1* 6/2006 Darrow et al. ................. 435/6

OTHER PUBLICATIONS

Protein structure prediction- Wikipedia, downloaded Oct. 14, 2005.*
Tertiary structures- Biology Pages, downloaded Oct. 14, 2005.*
Smith et al, Surface point mutations that significantly alter the structure and stability of a protein's denatured state, Protein Science, 1996, vol. 5, pp. 2009-2019.*
Q62627 downloaded from NCBI Jan. 6, 2007.*
BAC99030 downloaded from NCBI Jan. 6, 2007.*
NP_002574 downloaded from NCBI Jan. 6, 2007.*
AAD45355 downloaded from NCBI Jan. 6, 2007.*
Guo et al, Par-4 is a mediator of neuronal degeneration associated with the pathogenesis of Alzheimer disease, Nature Medicine, 1998, vol. 4(8), p. 957-962).*
Sells, et al., Commonality of the Gene Programs Induced by Effectors of Apoptosis in Androgen-dependent and independent Prostate Cells, Cell Growth & Differentiation, pp. 457-466, 1994.

* cited by examiner

*Primary Examiner*—Maria Marvich
(74) *Attorney, Agent, or Firm*—Crowell & Moring LLP

(57) ABSTRACT

The present invention relates to Par-4 mutants which cause apoptosis in cancer cells which are sensitive to Par-4 and also induce apoptosis in cancer cells which are resistant to Par-4. The present invention also relates to methods of using the Par-4 mutant to treat certain cancers, as well as to kits, vectors, and polypeptides for same.

4 Claims, 5 Drawing Sheets

FIG. 2A
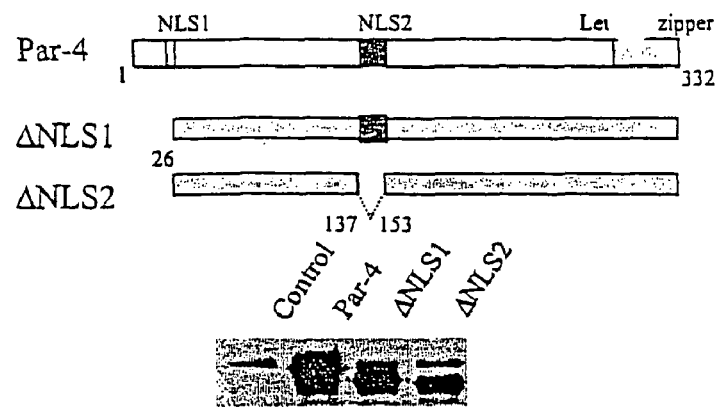
FIG. 2B
FIG. 2C
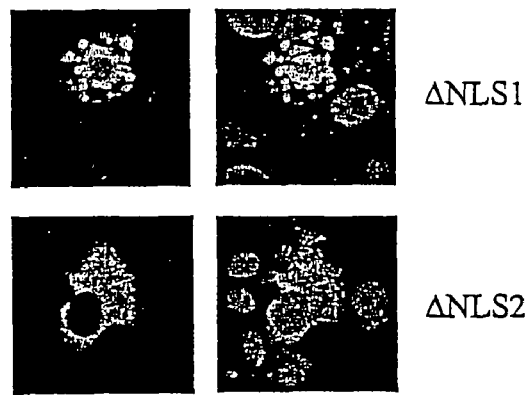
FIG. 2D
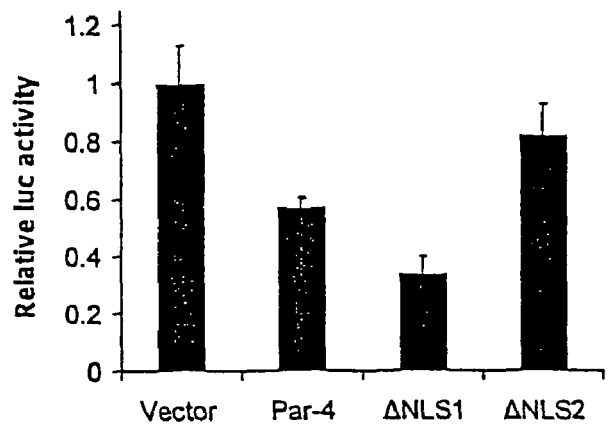
FIG. 2E
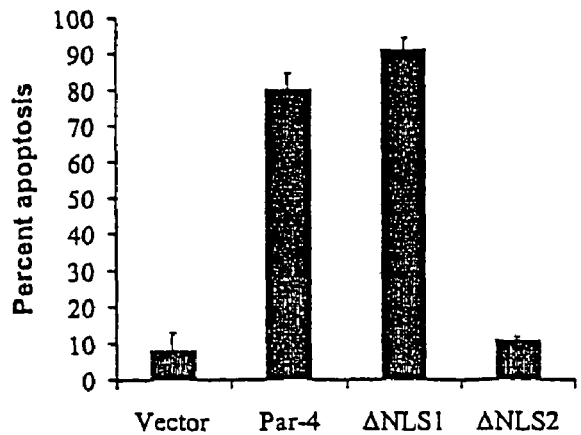

FIG. 4A
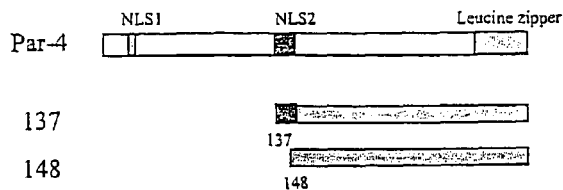
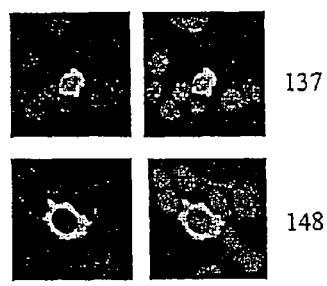
FIG. 4B
FIG. 4C
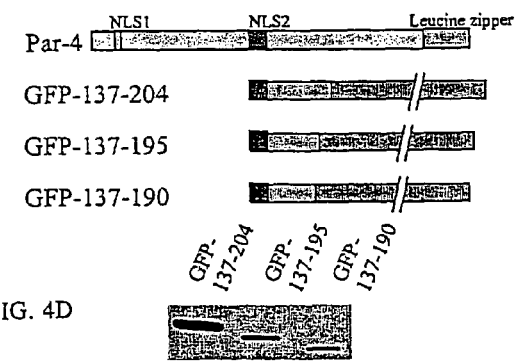
IG. 4D
FIG. 4E
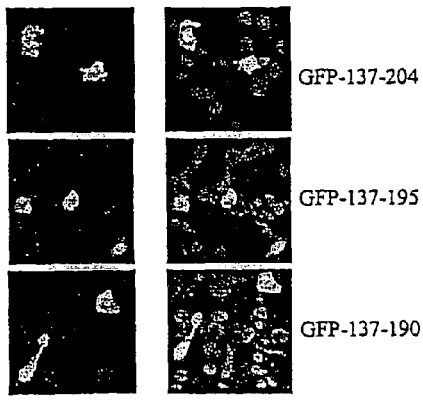
FIG. 4F
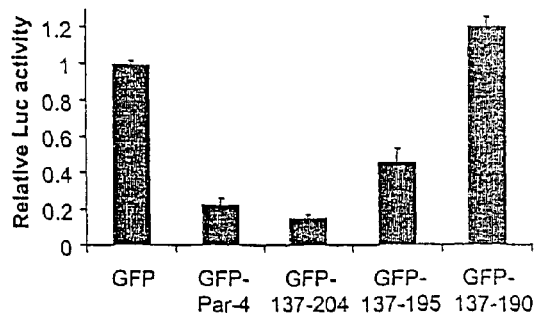
FIG. 4G
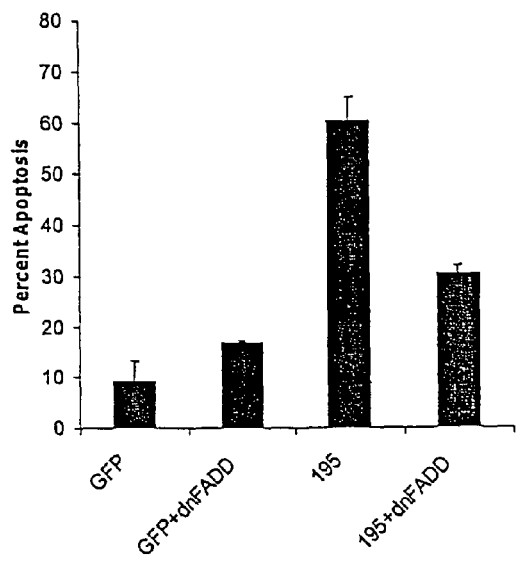

SEQUENCE LISTING

<160> NUMBER OF SEQ ID NOS: 1

<210> SEQ ID NO 1
<211> LENGTH: 332
<212> TYPE: PRT
<213> ORGANISM: Rattus norvegicus

<400> SEQUENCE: 1

Met Ala Thr Gly Gly Tyr Arg Ser Ser Gly Thr Thr Asp Phe Leu
1               5                   10                  15

Leu Trp Lys Ala Lys Arg Glu Lys Met Arg Ala Lys Gln Asn Pro Val
            20                  25                  30

Gly Pro Gly Ser Ser Gly Gly Asp Pro Ala Ala Lys Ser Pro Ala Gly
            35                  40                  45

Pro Leu Ala Gln Thr Thr Ala Ala Gly Thr Ser Glu Leu Asn His Gly
        50                  55                  60

Pro Ala Gly Ala Ala Ala Pro Ala Ala Pro Gly Pro Gly Ala Leu Asn
65                  70                  75                  80

Cys Ala His Gly Ser Ser Ala Leu Pro Arg Gly Ala Pro Gly Gly Ser
                85                  90                  95

Arg Arg Pro Glu Asp Glu Cys Pro Ile Ala Ala Gly Ala Ala Gly Ala
            100                 105                 110

Pro Ala Ser Arg Gly Asp Glu Glu Pro Asp Ser Ala Pro Glu Lys
        115                 120                 125

Gly Arg Ser Ser Gly Pro Ser Ala Arg Lys Gly Lys Gly Gln Ile Glu
130                 135                 140

Lys Arg Lys Leu Arg Glu Lys Arg Arg Ser Thr Gly Val Val Asn Ile
145                 150                 155                 160

Pro Ala Ala Glu Cys Leu Asp Glu Tyr Glu Asp Asp Glu Ala Gly Gln
                165                 170                 175

Lys Glu Arg Lys Arg Glu Asp Ala Ile Thr Gln Gln Asn Thr Ile Gln
            180                 185                 190

Asn Glu Ala Ala Ser Leu Pro Asp Pro Gly Thr Ser Tyr Leu Pro Gln
        195                 200                 205

Asp Pro Ser Arg Thr Val Pro Gly Arg Tyr Lys Ser Thr Ile Ser Ala
210                 215                 220

Pro Glu Glu Glu Ile Leu Asn Arg Tyr Pro Arg Thr Asp Arg Ser Gly
225                 230                 235                 240

Phe Ser Arg His Asn Arg Asp Thr Ser Ala Pro Ala Asn Phe Ala Ser
                245                 250                 255

Ser Ser Thr Leu Glu Lys Arg Ile Glu Asp Leu Glu Lys Glu Val Leu
            260                 265                 270

Arg Glu Arg Gln Glu Asn Leu Arg Leu Thr Arg Leu Met Gln Asp Lys
        275                 280                 285

Glu Glu Met Ile Gly Lys Leu Lys Glu Glu Ile Asp Leu Leu Asn Arg
290                 295                 300

Asp Leu Asp Asp Met Glu Asp Glu Asn Glu Gln Leu Lys Gln Glu Asn
305                 310                 315                 320

Lys Thr Leu Leu Lys Val Val Gly Gln Leu Thr Arg
                325                 330

IDENTIFICATION OF A UNIQUE CORE DOMAIN OF PAR-4 SUFFICIENT FOR SELECTIVE APOPTOSIS INDUCTION IN CANCER CELLS

CROSS-REFERENCE TO RELATED APPLICATIONS

This application claims priority under 35 U.S.C. §119 to U.S. Provisional Application No. 60/430,669 entitled "Identification of a Unique Core Domain of Par-4 Sufficient for Selective Apoptosis Induction in Cancer Cells" filed Dec. 4, 2002, the entire content of which is hereby incorporated by reference in its entirety.

IDENTIFICATION OF FEDERAL FUNDING

The present invention was supported by NIH/NCI R01 grants CA60872 and CA84511, and therefore the government may have rights in the invention.

FIELD OF THE INVENTION

The present invention relates to prostate apoptosis response-4 (Par-4) mutants which cause apoptosis in cancer cells which are sensitive to Par-4 and also induce apoptosis in cancer cells which are resistant to Par-4. The present invention also relates to methods of using the Par-4 mutant to treat certain cancers, as well as to kits, vectors, and polypeptides for same.

BACKGROUND OF THE INVENTION

These mutants/Par-4 may be effective against all cancers. Cancer causes the death of hundreds of thousands of people each year. Treatments for cancer are not always effective.

Cancer is difficult to treat because the development of cancer is a multistep process involving accumulation of multiple genetic aberrations. Most notable among such alterations is the loss of apoptotic responses that normally serve as built in checkpoints against the emergence of cell populations with dysfunctional traits or the acquisition of prosurvival mechanisms that override the apoptotic signals. The loss of apoptotic mechanisms often results in abridged response to cancer therapy. Therefore, alternate or combinatorial approaches to kill the cancer cells and induce tumor regression are often actively pursued by researchers and physicians.

Especially difficult to treat are those cancers which are hormonally related. These cancers include prostate cancer and breast cancer.

Prostate cancer is the most commonly diagnosed cancer in men and the second leading cause of cancer-related deaths in men in the United States. According to the American Cancer Society, about 198,100 new cases of prostate cancer will be diagnosed in the United States in 2001, and about 31,500 men will die of the disease. See www.cancer.org/docroot/STT/SH_0_2001.

Prostate cancer cells fall into two types: androgen dependent and androgen independent. Current treatment for prostate cancer involves hormone treatments that remove testosterone, thereby killing the prostate cancer cells that are dependent on the hormone. However, androgen independent cancer cells, which are the cells responsible for prostate cancer spreading to other areas, are not killed by this treatment. About 30 percent of patients develop androgen independent prostate cancer within three years of initial treatment, and patients with androgen independent cancer have a poor prognosis in both localized and disseminated disease. Currently, there is a 34% chance of recurrence of prostate cancer. The median time to development of clinical metastasis after biochemical recurrence is 8 years. Once treatment resistant metastatic disease is developed, the median time to death is an additional 5 years. Pound et al., *JAMA* (1999) 271: 1591-97.

Another common cancer linked to hormone action is breast cancer. Current treatments for breast cancer include surgery to remove the cancer, radiation therapy, chemotherapy, peripheral stem cell transplantation, bone marrow transplantation, hormonal therapy, and biological immunotherapy (using the immune system to fight cancer).

Side effects of cancer therapies are often severe. They include nausea, vomiting, pain, poor appetite, wasting, cachexia, diarrhea, burning in the stomach, stress, planter warts, nerve death-neuropathy, radiation burns, fatigue, constipation, anemia, anxiety, weakened immune system, dry skin, bone marrow suppression and hair loss.

An essential feature of anticancer strategies is the selective action against cancer cells, with little or no damage inflicted in normal cells. Identification of molecules that can specifically target tumor cells, therefore, appropriately constitutes a significant area of cancer research. Such molecules with selective action against tumor cells are valuable not only for their therapeutic potential; but also for their potential applications as tools for dissection of fundamental differences between normal and cancer cells. Thus, the identification of a molecule that can specifically target certain types of hormonally linked cancers would be extremely useful.

SUMMARY OF THE INVENTION

The present invention relates to the unexpected discovery of a unique domain of Par-4 (the SAC domain) which can cause apoptosis in previously resistant cancer cells, but not in normal cells. Certain Par-4 mutants have been discovered to be useful in the treatment of cancer.

An object of the present invention is to provide a modified Par-4 comprising a substitution of least one amino acid residue in the amino acid sequence of a precursor Par-4 in at least one position of naturally produced Par-4, wherein the modified Par-4 is effective in reducing the size of tumors resistant to Par-4. The modified Par-4 is preferably 1-204, 137-221, 137-213, 137-198 or 137-195.

Another object of the present invention provides an isolated nucleic acid sequence fragment comprising at least 500 contiguous nucleotides including a polymorphic site comprising a mutant of Par-4 selected from the group consisting of 1-204, 137-221, 137-213, 137-198 and 137-195. The invention also contemplates a recombinant DNA vector comprising one or more of these sequences operably linked to a transcription regulatory element. The invention further contemplates a cell comprising a DNA vector wherein the cell is preferably bacterial, fungal, plant, insect or mammalian. The invention further contemplates an isolated polypeptide comprising at least five amino acid residues, wherein the polypeptide has a sequence encoded by a nucleic acid contained in one or more sequences.

Another object of the present invention provides a method of producing a polypeptide, comprising incubating a host cell comprising a nucleic acid encoding a polypeptide under conditions that permit expression of the polypeptide. The method preferably comprises incubating a cell under conditions that permit expression of one or more polypeptides encoded by the nucleic acid.

Another object of the present invention provides an antibody that specifically binds to at least one immunogenic component, wherein the immunogenic component is encoded by one or more sequences of a Par-4 mutant.

Another object of the present invention provides a method of screening for therapeutic agents comprising selecting a Par-4-associated specific sequence as a target sequence; contacting a test compound with the target sequence; and selecting as candidate therapeutic agents those test compounds which bind to the target sequence.

The sequence is preferably a polypeptide encoded by a Par-4 mutant. The invention further contemplates a therapeutic compound comprising an agent which binds to one or more sequences of Par-4 mutant or a polypeptide encoded thereby.

Another object of the present invention provides a kit for detecting the presence of a Par-4 mutant-associated nucleic acid in a sample comprising at least one container means having disposed therein at least a first nucleic acid molecule of a Par-4 mutant. Preferably, at least one of the first and second nucleic acid molecule includes a detectable label.

Another object of the present invention provides a kit for detecting the presence a Par-4 mutant-associated polypeptide in a sample comprising at least one container means having disposed therein a first antibody specific for at least one polypeptide of a Par-4 mutant. The kit preferably comprises a second antibody specific for at least one polypeptide of a Par-4 mutant. The kit preferably further comprises a means for detecting at least one of the first and second antibodies.

Another object of the present invention provides a method of treating cancer in a subject suffering therefrom, comprising administering to the subject a Par-4 mutant, wherein the administration of the Par-4 mutant causes reduction of tumors resistant to Par-4. The types of cancer treated include, but are not limited to, prostate cancer, breast cancer and lung cancer, and head and neck tumors. The subject is preferably a canine, a feline, an ovine, a primate, an equine, a porcine, a caprine, a camelid, an avian, a bovine, amphibian, fish or a murine organism. The subject is preferably a primate. The primate is preferably human. The Par-4 mutant is preferably 1-204, 137-221, 137-213, 137-198 and 137-195.

Another object of the present invention provides a pharmaceutical composition for the treatment of cancer, comprising an isolated and purified Par-4 mutant and a pharmaceutically acceptable diluent, carrier or excipient.

The mode of expression of the mutants in the cancer cells may include, but not limited to, the use of adenoviral vectors that can be injected intratumorally or intravenously, or as peptides or as fusion with other proteins or with antibodies. The use of these mutants can be combined with other forms of cancer treatment including, but not limited to, hormone therapy, chemotherapy or ionizing radiation.

BRIEF DESCRIPTION OF THE DRAWINGS

FIG. 2 shows that the NLS2 is required for nuclear entry, inhibition of NF-B activity and induction of apoptosis. A schematic representation of full length Par-4, NLS1 and NLS2 is shown in panel A. PC-3 cells were transiently transfected with vector control, Par-4, NLS 1 or NLS2 or their GFP-tagged derivatives. The expression of endogenous Par-4 (control), and ectopic Par-4, NLS1 and NLS2 proteins were examined by Western blot analysis (B). Intracellular localization of NLS 1 and NLS2 (C), and their ability to induce apoptosis (E), were examined as indicated in the description of FIG. 1. The apoptotic morphology of the NLS1 transfected cell in panel CTo determines the inhibition of NF-B transcriptional activity by Par-4 or its mutants (D). Cells were transfected for 48 hours with a Re1A reporter system and -galactosidase plasmid together with vector, Par-4 or mutant constructs. Lysates were subjected to luciferase assays, and luciferase activity was normalized to the corresponding galactosidase activity. Inhibition of luciferase activity by Par-4 or its mutants is expressed relative to the activity noted with vector.

FIG. 4 shows the identification of the core domain of Par-4 which is sufficient for apoptosis. Cells were transiently transfected with GFP-tagged derivatives of Par-4 deletion mutant 137-332 or 148-332 (A) and examined for intracellular localization (B). Cells were transiently transfected with various deletion mutants of Par-4 137-204, 137-195, 137-190 or their GFP-tagged derivatives (C), and examined for expression by Western blot analysis (D), intracellular localization (E), inhibition of NF-B activity (F), and apoptosis induction in the presence or absence of ectopic dnFADD (G), as seen in FIG. 1.

DETAILED DESCRIPTION OF THE INVENTION

A. Definitions

Figure 1A:
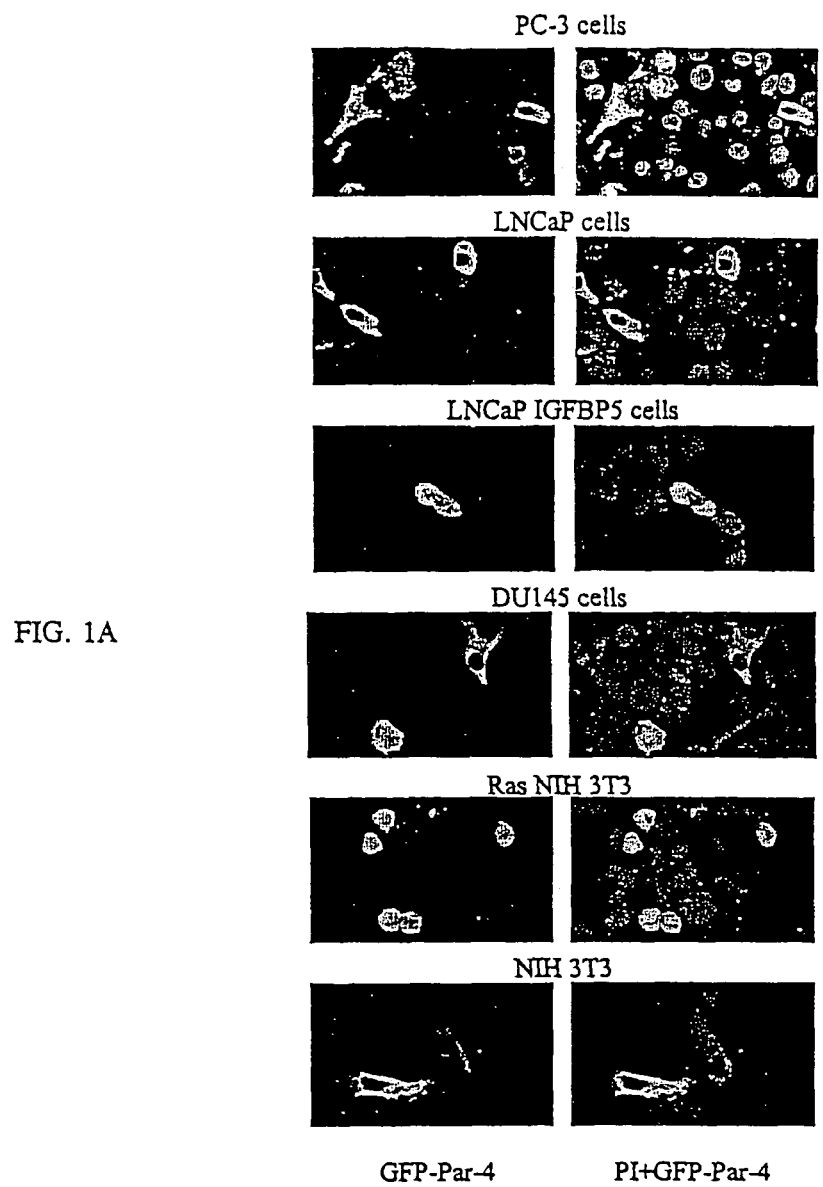
FIG. 1 shows the nuclear localization of Par-4 correlates with apoptosis induction. Cells were transfected with GFP-Par-4 and treated with propidium iodide (PI) to detect nuclei. Intracellular localization of GFP-Par-4 was recorded by confocal microscopy (A). GFP-Par-4 images are shown in the left panel, and the overlay of the GFP-Par-4 and PI images are shown in right panel. The yellow color, resulting from the co-localization of GFP green fluorescence with reddish-orange PI staining (right panel), indicates the nuclear expression of Par-4. To determine percentage of apoptosis, cells were transfected with GFP-Par-4 or GFP-vector as the control, and then subjected to DAPI staining. Apoptotic cells were quantified and expressed as a percentage of the total number of transfected cells (B).

In general, the terms in the present application are used consistently with the manner in which those terms are understood in the art.

By "androgen-independent" is meant cancer cells or tumors which do not require androgen to progress and/or proliferate.

By "expression vector" is meant a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. The invention is intended to include such other forms of expression vectors which serve equivalent functions and which are, or become, known in the art.

Host cells are transformed or transfected with vectors constructed using recombinant DNA techniques. Such transformed host cells are capable of either replicating vectors encoding the carbonyl hydrolase mutants or expressing the desired carbonyl hydrolase mutant. In the case of vectors which encode the pre or prepro form of the carbonyl hydrolase mutant, such mutants, when expressed, are typically secreted from the host cell into the host cell medium.

By "operably linked" is meant the relationship between two DNA regions such that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring Par-4 may be obtained in accord with the general methods described by methods known in the art.

The cloned Par-4 may then be used to transfect a host cell in order to express the Par-4. The Par-4 gene may then be ligated into a high copy number plasmid. This plasmid replicates in hosts in the sense that it contains the well-known elements necessary for plasmid replication; a promoter operably linked to the gene in question (which may be supplied as the gene's own homologous promoter if it is recognized, i.e., transcribed, by the host), a transcription termination and polyadenylation region (necessary for stability of the mRNA transcribed by the host from the Par-4 gene in certain eucaryotic host cells) which is exogenous or is supplied by the endogenous terminator region of the Par-4 gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the Par-4 gene into host genome. This is facilitated by procaryotic and eucaryotic organisms which are particularly susceptible to homologous recombination.

II. Introduction

The inventors have discovered that various in vitro mutations involving the deletion of one or more amino acids within a Par-4 amino acid sequence can confer advantageous properties to such mutants especially with regard to inducing cancer cell death.

Specifically, the Par-4 gene has been mutated by modifying the DNA to encode the substitution of one or more amino acids at various amino acid residues within the mature form of the Par-4 molecule.

The inventors have discovered that nuclear translocation of Par-4 correlates with susceptibility to apoptosis. Specifically, a unique core domain of Par-4 which is required for the induction of apoptosis has been discovered. This core domain induces apoptosis in cancer cells, but not in normal cells.

The inventors have discovered the following important mutants of Par-4. In summary, the following mutants have been unexpectedly found to induce apoptosis in cancer cells which are sensitive or resistant to full-length Par-4 (SEQ ID NO: 1), but do not induce apoptosis in normal cells. They are 1-204, 137-221, 137-213, 137-198 and 137-195 of SEQ ID NO: 1. One advantage of these mutants is that they define the active domain of Par-4 and localize that active domain to the 59 amino acid region between amino acid 137 and 195 of Par-4 (the wild type Par-4 has 332 amino acids, SEQ ID NO: 1). This 59 amino acid region contains a nuclear localization sequence that allows entry of the protein into the nucleus and two phosphorylation sites. Thus, these mutants are useful in inducing apoptosis in cancer cells.

III. Par-4 Mechanism of Action

The Par-4 gene, first identified by the inventors (see Sells et al., 1994) in prostate cancer cells undergoing apoptosis, encodes a proapoptotic protein that is remarkably effective in inducing cancer cell apoptosis and tumor regression in animal models. The inventors have found that Par-4 induces apoptosis in androgen independent prostate cancer cells, such as PC3 and DU145, and in Ras transformed mouse fibroblasts. However, Par-4 does not induce apoptosis in androgen dependent prostate cancer cells, such as LNCaP, in immortalized cells or in primary cultures of normal prostate epithelial and stromal cells.

Overexpression of Par-4 in cells that are resistant to direct apoptosis by Par-4 renders the cells supersensitive to a broad range of apoptotic insults, including chemotherapeutic agents, TNF, or ionizing radiation. The Par-4 gene maps to human chromosome 12q21, which is often deleted in pancreatic cancer. Par-4 expression is downregulated in renal cell carcinoma relative to the normal proximal tubular cell compartment. Moreover, oncogenes such as Ras, Raf or Src downregulate Par-4 expression, and restoration of Par-4 level results in inhibition of oncogene induced transformation of cells. Inhibition of Par-4 with a dominant negative mutant or an antisense oligodeoxynucleotide has been found to protect neuronal cells from apoptosis in cell culture and animal models of neurodegenerative diseases.

The transcription activity of NFkB is an essential antiapoptotic target of Par-4. NfkB plays a crucial role in inflammation and immune response by activating the transcription of a number of key cytokines and cytokine receptors, antagonizing apoptosis by upregulation of inhibitor of apoptosis proteins and supporting cell proliferation. More importantly, NFkB plays an essential role in oncogenesis and in the resistance of tumor cells to ionizing radiation and chemotherapy. The transcription potential of NFkB, a heterodimer between subunits p65 (RelA) and p50, is fully activated by translocation to the nucleus and phosphorylation of RelA. Par-4 inhibits Ras or Raf induced NFkB transcriptional activity in mouse fibroblast cells and the constitutively activated NFkB transcription activity in androgen independent prostate cancer cell lines.

Previous studies indicated that the inhibitory effect of Par-4 is targeted toward the transactivation domain (TA1) of the RelA subunit of NFkB. Inhibition of NFkB activity by super-repressor IkBa is sufficient to induce apoptosis in NIH 3T3 cells expressing oncogenic Ras. Overexpression of Par-4 is sufficient to induce apoptosis in these cells. However, in androgen independent prostate cancer cells, inhibition of NFkB is not sufficient to induce apoptosis or to cause tumor regression, suggesting that Par-4 may also activate a prodeath pathway in these cells.

Par-4 was found to induce apoptosis by coparallel activation of the FasL/Fas pathway and inhibition of NFkB transcription activity in the androgen independent cells. Fas (CD95) is a member of the TNFR family of death receptors that is activated by binding to FasL leading to the formation of DISC. This complex is composed of the trimerized Fas, FADD and procaspase 8 and its formation leads to the activation of caspase8 and to the induction of downstream caspases and apoptosis. Specifically, Par-4 activates the Fas pathway by promoting the Fas/FasL translocation to the cell membrane and by protecting the Fas apoptotic pathway from the inhibitory effects of zPKC. Activation of the Fas pathway and inhibition of NFkB activity are both essential for apoptosis induction by Par-4 in androgen independent prostate cancer cells.

Despite the advances made in understanding the mechanism of action of Par-4, the active domains of Par-4, as well as its functional localization, were largely unknown. The amino acid sequence of the Par-4 protein predicts a leucine zipper domain at its C-terminal end, between amino acids 292 and 332. This domain is involved in binding to all currently known partners of Par-4, including WT1, zPKC, p62 and Dlk. The leucine zipper domain is required for sensitization to apoptosis by Par-4. A deletion mutant of Par-4 lacking the leucine zipper domain (DZip) is unable to sensitize cells to apoptotic stimuli. Moreover, PC12 cells expressing DZip are insensitive to Ab142 or withdrawal of trophic factors. These findings indicate that the C-terminal leucine zipper domain is indispensable for the apoptosis sensitizing function of Par-4 (see Sells et al. 1997).

Par-4 contains two putative nuclear localization sequences, NLS1 at amino acids 20 to 25 and NLS2 at amino acids 137-153, both in the N terminal half of Par-4. In most tissues and cell types, endogenous Par-4 is localized in the cytoplasm. Par-4 is cytoplasmic in the immortalized fibroblast cells NIH 3T3, and deletion of the first 68 amino acids including NLS1 does not affect the apoptosis sensitizing function of Par-4. The following observations support a nuclear function for Par-4: (1) the presence of a bipartite nuclear localization sequence (NLS2); (2) the ability of Par-4 to inhibit RelA transcription activity; (3) direct binding to the nuclear proteins Dlk and WT1; and (4) binding to WT1 and inhibition of the bcl2 promoter.

Recent studies indicate that the leucine zipper domain protein Par-4 induces apoptosis in certain cancer cells by activation of the Fas prodeath receptor pathway and coparallel inhibition of the cell survival NFkB transcription activity. However, the intracellular localization or functional domains of Par-4 involved in apoptosis remained unknown.

In the present invention, structure function analysis indicated that inhibition of NFkB transcription activity and apoptosis are dependent on Par-4 translocation to the nucleus via a bipartite nuclear localization signal sequence NLS2. Cancer cells that were resistant to Par-4 induced apoptosis retained Par-4 in the cytoplasm. A 59 amino acid core from amino acids 137 to 195 that included NLS2, but not the C-terminal leucine zipper domain of Par-4, was necessary and sufficient to induce Fas pathway activation, inhibition of nuclear NFkB transcription activity and apoptosis. Most importantly, this core domain of Par-4 had an expanded apoptotic target range extending to the cancer cells that were resistant to Par-4, but not to normal cells. These findings have identified a unique 'death domain' that is selective for apoptosis induction in cancer cells, (i.e., the SAC domain), which holds promise for identifying key differences between cancer and normal cells, and for molecular therapy of cancer.

Thus, the present invention indicates that Par-4 translocation into the nucleus is essential for induction of apoptosis. The NLS2 domain of Par-4 is essential for nuclear translocation, and resistance to apoptosis was noted in cells that did not translocate Par-4 to the nucleus or with Par-4 constructs that lacked an intact NLS2 domain. Moreover, nuclear translocation was essential for inhibition of RelA transcription activity by Par-4. Because inhibition of RelA activity is critical for apoptosis by Par-4, these observations suggest that Par-4 has a nuclear function that includes RelA transcription inhibition and induction of apoptosis. Further, the deletion analysis identified the 59 amino acid core domain of Par-4 that constitutes a minimal region of Par-4 which is sufficient for apoptosis. This core domain translocates into the nucleus in both cancer and normal or immortalized cells, but is selective in inducing apoptosis of the cancer cells, regardless of whether or not they are sensitive to wild type Par-4. This core domain is 100% conserved in rat, mouse and human Par-4. Because this domain does not induce apoptosis in normal cells but induces apoptosis in diverse cancer cells, it has been designated Selective Apoptosis induction of Cancer cells (i.e., SAC domain). This domain does not resemble the death domains (DD) or death effector domains (DED) of other proapoptotic proteins. Unlike the previously characterized DD/DED, the SAC domain specifically induces apoptosis in cancer cells and not normal cells. Because Par-4 causes remarkable regression of solid tumors by apoptosis driven by Fas pro-death pathway activation and inhibition of NFkB activity, the SAC domain, which utilizes a similar mechanism of apoptosis, also causes tumor regression by apoptosis. The cancer specific apoptotic potential of the SAC domain renders it a promising candidate for directed molecular therapeutics of cancer.

The leucine zipper domain of Par-4 is necessary for apoptosis sensitization of cells to diverse apoptotic insults (see Sells et al., 1997). This sensitizing action is regulated by Par-4 interaction via its leucine zipper domain, with WT1, DLK, zPKC, and p62. Depending on the partner and the cellular context, the apoptosis sensitizing function of Par-4 is implemented in the cytoplasm when regulated by DLK, zPKC, and p62, or in the nucleus when regulated by WT1. The findings of the present invention suggest that the leucine zipper domain of Par-4 is not essential for apoptosis induced by Par-4 acting alone. Thus, the interactive partners identified thus far might not be involved in regulation of the direct apoptotic action of Par-4, unless they also bind to the core domain. In addition, the deletion of the leucine zipper domain resulted in increased nuclear translocation of Par-4. Because the leucine zipper domain contains a putative nuclear exclusion sequence (amino acids 291 to 302) that may compete with NLS2 sequence, it is believed that the distribution of Par-4 in the nuclear versus cytoplasmic compartments may be regulated by the relative activities of the NES and NLS2 domains.

In summary, by deletion analysis, the present invention provides a unique core domain of Par-4 that is essential for nuclear entry, Fas pro-death pathway activation, inhibition of NFkB activity and induction of apoptosis. This domain extends the susceptibility spectrum of Par-4 to diverse cancer cells, regardless of whether they are susceptible or resistant to Par-4. Because this domain shows selective action against cancer cells but not normal cells, it has both academic and therapeutic applications.

IV. Mutants of Par-4

The inventors have discovered the following important mutants of Par-4. In summary, the following mutants have been unexpectedly found to induce apoptosis in cancer cells which are sensitive or resistant to full-length Par-4, but do not induce apoptosis in normal cells. They are 1-204, 137-221, 137-213, 137-198 and 137-195. One advantage of these mutants is that they define the active domain of Par-4 and localize that active domain to the 59 amino acid region between amino acid 137 and 195 of Par-4 (the wild type Par-4 has 332 amino acids). This 59 amino acid region contains a nuclear localization sequence that allows entry of the protein into the nucleus and two phosphorylatron sites. Thus, these mutants are useful in inducing apoptosis in cancer cells.

Those of ordinary skill in the art will recognize that the particular methods of polymorphism identification described herein are not intended to be limiting of the present invention. Any of the variety of other known techniques, such as, for example, RNA-DNA hybrid cleavage using RNase A, mismatch detection using heteroduplex analysis, denaturing gradient electrophoresis, and chemical cleavage heteroduplex DNA (see, Current Protocols in Human Genetics, Volume 1, Chapter 7, John Wiley and Sons, 1995).

As described above, the present invention relates to Par-4 sequences, RNA, fragments of the genomic, cDNA, or nucleic acids comprising 5, 10, 15, 30, 60, 100, 200, 500 or more contiguous nucleotides, and the complements thereof. Closely related variants are also included as part of this invention, as well as recombinant nucleic acids comprising at least 50, 60, 70, 80, or 90% of the nucleic acids described above which would be identical to the Par-4 nucleic acids except for one or a few substitutions, deletions, or additions.

Further, the nucleic acids of this invention include the adjacent chromosomal regions of Par-4 required for accurate expression of the respective gene. In a preferred embodiment, the present invention is directed to at least 15 contiguous nucleotides of the nucleic acid sequence of Par-4.

It is understood that, as a result of the degeneracy of the genetic code, many nucleic acid sequences are possible which encode a Par-4-like protein or polypeptide. Some of these will have little homology to the nucleotide sequences of any known or naturally-occurring Par-4-like gene but can be used to produce the proteins and polypeptides of this invention by selection of combinations of nucleotide triplets based on codon choices. Such variants, while not hybridizable to a naturally occurring Par-4 gene, are contemplated within this invention.

The nucleic acids described herein are used in the methods of the present 30 invention for production of proteins or polypeptides, through incorporation into cells, tissues, or organisms. In one embodiment, DNA containing all or part of the coding sequence for a Par-4 polypeptide, or DNA which hybridizes to DNA, is incorporated into a vector for expression of the encoded polypeptide in suitable host cells. The encoded polypeptide consisting of Par-4, or its functional equivalent is capable of normal activity. The term "vector" as used herein refers to a nucleic acid molecule capable of transporting another nucleic acid to which it has been linked. A vector, for example, can be a plasmid.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated", as used herein, refers to nucleic or amino acid sequences that are at least 60% free, preferably 75% free, and most preferably 90% free from other components with which they are naturally associated. "Isolated" nucleic acids (polynucleotides) include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow or make probable a desired recombination event. Portions of the isolated nucleic acids which code for polypeptides having a certain function can be identified and isolated by methods known in the art.

A further embodiment of the invention is antisense nucleic acids or oligonucleotides which are complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acids or oligonucleotides can inhibit the expression of the gene encoded by the sense strand or the mRNA transcribed from the sense strand. Antisense nucleic acids can be produced by standard techniques known in the art.

In a particular embodiment, an antisense nucleic acid or oligonucleotide is wholly or partially complementary to and can hybridize with a target nucleic acid (either DNA or RNA), wherein the target nucleic acid can hybridize to a nucleic acid having the sequence of the complement of the strand. For example, an antisense nucleic acid or oligonucleotide can be complementary to a target nucleic acid having the sequence shown as the strand of the open reading frame or nucleic acid encoding a functional equivalent of Par-4, or to a portion of these nucleic acids sufficient to allow hybridization. A portion, for example, a sequence of 16 nucleotides could be sufficient to inhibit expression of the protein. Or, an antisense nucleic acid or oligonucleotide complementary to 5' or 3' untranslated regions, or overlapping the translation initiation codon (5' untranslated and translated regions), of the Par-4 gene, or a gene encoding a functional equivalent can also be effective. In another embodiment, the antisense nucleic acid is wholly or partially complementary to and can hybridize with a target nucleic acid which encodes a Par-4 polypeptide.

In addition to the antisense nucleic acids of the invention, oligonucleotides can be constructed which will bind to duplex nucleic acid either in the gene or the DNA:RNA complex of transcription, to form a stable triple helix-containing or triplex nucleic acid to inhibit transcription and/or expression of a gene encoding Par-4, or its functional equivalent. Such oligonucleotides of the invention are constructed using the base-pairing rules of triple helix formation and the nucleotide sequence of the gene or mRNA for Par-4. These oligonucleotides can block Par-4-type activity in a number of ways, including prevention of transcription of the Par-4 gene or by binding to mRNA as it is transcribed by the gene.

The invention also relates to proteins or polypeptides encoded by the nucleic acids described herein. The proteins and polypeptides of this invention can be isolated and/or recombinant. Proteins or polypeptides referred to herein as "isolated" are proteins or polypeptides purified to a state beyond that in which they exist in cells. In a preferred embodiment, they are at least 10% pure; i.e., most preferably they are substantially purified to 80 or 90% purity. "Isolated" proteins or polypeptides include proteins or polypeptides obtained by methods described infra, similar methods or other suitable methods, and include essentially pure proteins or polypeptides, proteins or polypeptides produced by chemical synthesis or by combinations of biological and chemical methods, and recombinant proteins or polypeptides which are isolated. Proteins or polypeptides referred to herein as "recombinant" are proteins or polypeptides produced by the expression of recombinant nucleic acids. In a preferred embodiment, the protein or portion thereof has at least one function characteristic of a Par-4 protein or polypeptide.

A "portion" as used herein with regard to a protein or polypeptide, refers to fragments of that protein or polypeptide. The fragments can range in size from 5 amino acid residues to all but one residue of the entire protein sequence. Thus, a portion or fragment can be at least 5, 5-50, 50-100, 100-200, 200-400, 400-800, or more 20 consecutive amino acid residues of a Par-4 protein or polypeptide, for example, Table 2, or a variant thereof. The invention also relates to isolated, synthesized and/or recombinant portions or fragments of a Par-4 protein or polypeptide as described above. Polypeptide fragments of the enzyme can be made which have full or partial function on their own, or which when mixed together (though fully, partially, or nonfunctional alone), spontaneously assemble with one or more other polypeptides to reconstitute a functional protein having at least one functional characteristic of a Par-4 protein of this invention.

The invention also concerns the use of the nucleotide sequence of the nucleic 30 acids of this invention to identify DNA probes for Par-4 genes, PCR primers to amplify Par-4 genes, and regulatory elements of the Par-4 genes.

The nucleic acids of this invention can be produced in large quantities by replication in a suitable host cell. Natural or synthetic nucleic acid fragments, comprising at least ten contiguous bases coding for a desired peptide or polypeptide can be incorporated into recombinant nucleic acid constructs, usually DNA constructs, capable of introduction into and replication in a prokaryotic or eukaryotic cell. Usually the nucleic acid constructs will be suitable for replication in a unicellular host, such as yeast or bacteria, but may also be intended for introduction to (with and without integration within the genome) cultured mammalian or plant or other eukaryotic cells, cell lines, tissues, or organisms. The purification of nucleic acids produced by the methods of the present invention is described, for example, in Sambrook et al, *Molecular Cloning. A Laboratory Manual*, 2nd Ed. (Cold Spring Harbor Laboratory, Cold Spring Harbor, N.Y. (1989) or Ausubel et al, *Current Protocols in Molecular Biology*, J. Wiley and Sons, NY (1992).

The nucleic acids of the present invention can also be produced by chemical synthesis, e.g., by the phosphoramidite method described by Beaucage et al., *Tetra. Letts.*, 22:1859-1862 (1981) or the triester method according to Matteucci et al., *J. Am. Chem. Soc.*, 103:3 185 (1981), and can performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

These nucleic acids can encode full-length variant forms of proteins as well as the naturally-occurring protein. The variant proteins (which could be especially useful for detection and treatment of disorders) will have the variant amino acid sequences encoded by polymorphisms, when said polymorphisms are read so as to be in-frame with the full-length coding sequence of which it is a component.

Nucleic acid constructs prepared for introduction into a prokaryotic or eukaryotic host will comprise a replication system recognized by the host, including the intended nucleic acid fragment encoding the selected protein or polypeptide, and will preferably also include transcription and translational initiation regulatory sequences operably linked to the protein encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals are also included, where appropriate, whether from a native Par-4 protein or from other receptors or from secreted proteins of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook et al., *Molecular Cloning. A Laboratory Manual*, 2nd Ed. (Cold Spring Harbor Laboratory, Cold Spring Harbor, N.Y. (1989) or Ausubel et al., *Current Protocols in Molecular Biology*, J. Wiley and Sons, NY (1992).

An appropriate promoter and other necessary vector sequences will be selected 15 so as to be functional in the host, and will include, when appropriate, those naturally associated with Par-4 genes. Examples of workable combinations of cell lines and expression vectors are described in Sambrook et al., *Molecular Cloning A Laboratory Manual*, 2nd Ed. (Cold Spring Harbor Laboratory, Cold Spring Harbor, N.Y. (1989) or Ausubel et al., *Current Protocols in Molecular Biology*, J. Wiley and Sons, NY (1992). Many useful vectors are known in the art and can be obtained from such vendors as Stratagene (supra), New England BioLabs, Beverly, Mass., U.S.A, Promega Biotech, and other biotechnology product suppliers. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. In addition, the construct may be joined to an amplifiable gene so that multiple copies of the gene may be made. For appropriate enhancer and other expression control sequences, see also *Enhancers and Eukaryotic Gene Expression*, Cold Spring Harbor Press, Cold Spring Harbor, N.Y. (1983). While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., *FEBS Letts.* 241:119 (1988)), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See, Sambrook et al., 1989 and Ausubel et al., 1992. The introduction of the nucleic acids into the host cell by any method known in the art, including those described above, will be referred to herein as "transformation." The cells into which have been introduced nucleic acids described above are meant to also include the progeny of such cells.

Large quantities of the nucleic acids and proteins of the present invention may be prepared by expressing the Par-4 nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or *Pseudomonas* may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.), *Cell Culture. Methods in Enzymology*, volume 58, Academic Press, Inc., Harcourt Brace Jovanovich, N.Y., (1979)). Examples of commonly used mammalian host cell lines are VERO and HeLa cells, Chinese hamster ovary (CHO) cells, and W138, BHK, and CQS cell lines, although it will be appreciated by the skilled practitioner that other cell lines may be appropriate, e.g., to provide higher expression desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the nucleic acids of the present invention will be useful not only for the production of the nucleic acids and proteins of the present invention, but also, for example, in studying the characteristics of Par-4 proteins.

Antisense nucleic acid sequences are useful in preventing or diminishing the expression of Par-4 genes, as will be appreciated by one skilled in the art. For example, nucleic acid vectors containing all or a fragment of Par-4 genes, complementary sequences of the former may be placed under the control of a promoter in an antisense orientation and introduced into a cell. Expression of such an antisense construct within a cell will interfere with Par-4 transcription and/or translation and/or replication.

The probes and primers based on the Par-4 gene sequences disclosed herein are used to identify homologous Par-4 gene sequences and proteins in other species. These Par-4 gene sequences and proteins are used in the diagnostic/prognostic, therapeutic and drug screening methods described herein for the species from which they have been isolated.

Expression and purification of the Par-4 proteins of the invention can be performed essentially as outlined below. To facilitate the cloning, expression and purification of membrane and secreted protein a gene expression system, such as the pET System (Novagen), for cloning and expression of recombinant proteins in *E. coli* is selected. Also, a DNA sequence encoding a peptide tag, the His-Tap, is fused to the 3' end of DNA sequences of interest to facilitate purification of the recombinant protein products. The 3 end is selected for fusion to avoid alteration of any 5' terminal signal sequence.

Nucleic acids chosen, for example, from the nucleic acids set forth in Table 2 for cloning the genes are prepared by polymerase chain reaction (PeR). Synthetic oligonucleotide primers specific for the 5 and 3 ends of the nucleotide sequences are designed and purchased from Life Technologies (Gaithersburg, Md.). All forward primers (specific for the 5' end of the sequence) are designed to include an NcoI cloning site at the 5' terminus. These primers are designed to permit initiation of protein translation at the methionine residue encoded within the NcoI site followed by a valine residue and the protein encoded by the DNA sequence. All reverse primers (specific for the 3' end of the sequence) include an EcoRI site at the 5' terminus to permit cloning of the sequence into the reading frame of the pET-28b. The pET-28b vector provides a sequence encoding an additional 20 carboxyl-terminal amino acids including six histidine residues (at the C-terminus), which comprise the histidine affinity tag.

Genomic DNA prepared from an individual as described in Example 1 is used as the source of template DNA for PCR amplification (Ausubel et al., *Current Protocols in Molecular Biology*, John Wilty & Sons (1994)). To amplify a DNA sequence containing the nucleotide sequence, genomic DNA (50 ng) is introduced into a reaction vial containing 2 mM $MgCl_2$, 1 micromolar synthetic oligonucleotide primers (forward and reverse primers) complementary to and flanking a defined Par-4 region, 0.2 mM of each of deoxynucleotide triphosphate, dATP, dGTP, dCTP, dTTP and 2.5 units of heat stable DNA polymerase (Amplitaq, Roche Molecular Systems, Inc., Branchburg, N.J.) in a final volume of 100 microliters.

Upon completion of thermal cycling reactions, each sample of amplified DNA is purified using the Qiaquick Spin PCR purification kit (Qiagen, Gaithersburg, Md.). All amplified DNA samples are subjected to digestion with the restriction endonucleases, e.g., NcoI and EcoRI (New England BioLabs, Beverly, Mass., U.S.A.) (Ausubel et al., *Current Protocols in Molecular Biology*, John Wiley & Sons, Inc. (1994)). DNA samples are then subjected to electrophoresis on 1.0% NuSeive (IFMC BioProducts, Rockland, Me.) agarose gels. DNA is visualized by exposure to ethidium bromide and long wave UV irradiation. DNA contained in slices isolated from the agarose gel are purified using the Bio 101 GeneClean Kit protocol (Bio 101, Vista, Calif.).

The pET-28b vector is prepared for cloning by digestion with restriction endonucleases, e.g., NcoI and EcoRI (New England BioLabs, Beverly, Mass.) (Ausubel et al., *Current Protocols in Molecular Biology*, John Wiley & Sons, Inc. (1994)). The pET-28a vector, which encodes the histidine affinity tag that can be fused to the 5 end of an inserted gene, is prepared by digestion with appropriate restriction endonucleases.

Following digestion, DNA inserts are cloned (Ausubel et al., *Current Protocols in Molecular Biology*, John Wiley &

Sons, Inc. (1994)) into the previously digested pET-28b expression vector. Products of the ligation reaction are then used to transform the BL21 strain of E. coil (Ausubel et al., Current Protocols in Molecular Biology, John Wiley & Sons, Inc. (1994)) as described below.

Competent bacteria, E. coli strain BL21 or E. coli strain BL21 (DE3), are transformed with recombinant pET expression plasmids carrying the cloned sequence according to standard methods (Ausubel et al., Current Protocols in Molecular Biology, John Wiley & Sons, Inc. (1994)). Briefly, 1 microliter of ligation reaction is mixed with 50 microliters of electrocompetent cells and subjected to a high voltage pulse, after which samples were incubated in 0.45 ml SOC medium (0.5% yeast extract, 2.0% tryptone, 10 mM NaC1, 2.5 mM KC1, 10 mM $MgCl_2$, 10 mM $MgSO_4$ and 20 mM glucose) at 37° C. with shaking for 1 hour. Samples are then spread on LB agar plates containing 25 g/ml kanamycin sulfate for growth overnight. Transformed colonies of BL21 are then picked and analyzed to evaluate cloned inserts, as described below.

The pET vector can be propagated in any E. coil K-12 strain, e.g., HNIS 174, HB1O1, JM1O9, DH5 and the like, for purposes of cloning or plasmid preparation. Hosts for expression include E. coil strains containing a chromosomal copy of the gene for T7 RNA polymerase. These hosts are lysogens of bacteriophage DE3, a lambda derivative that carries the lad gene, the lacUV5 promoter and the gene for T7 RNA polymerase. T7 RNA polymerase is induced by addition of isopropyl-D-thiogalactoside (IPTG), and the T7 RNA polymerase transcribes any target plasmid containing a functional T7 promoter, such as pET-28b, carrying its gene of interest. Strains include, for example, BL21 (DE3) (Studier et al., Meth. Enzymol., 185:60-89 (1990)).

To express the recombinant sequence, 50 ng of plasmid DNA are isolated as described above to transform competent BL21 (DE3) bacteria as described above (provided by Novagen as part of the pET expression kit). The lacZ gene (-galactosidase) is expressed in the pET-System as described for the Par-4 recombinant constructions. Transformed cells were cultured in SOC medium for 1 hour, and the culture is then plated on LB plates containing 25 µg/ml kanamycin sulfate. The following day, the bacterial colonies are pooled and grown in LB medium containing kanamycin sulfate (25 µg/ml) to an optical density at 600 nM of 0.5 to 1.0 O.D. units, at which point 1 mM IPTG was added to the culture for 3 hours to induce 30 gene expression of the Par-4 recombinant DNA constructions.

After induction of gene expression with IPTG, bacteria are collected by centrifugation in a Sorvall RC-3B centrifuge at 3500×g for 15 minutes at 4° C. Pellets are resuspended in 50 ml of cold mM Tris-HC1, pH 8.0, 0.1 M NaC1 and 0.1 mM EDTA (STE buffer). Cells are then centrifuged at 2000×g for 20 minutes at 4° C. Wet pellets are weighed and frozen at −80° C. until ready for protein purification.

A variety of methodologies known in the art can be used to purify the isolated proteins (Coligan et al., Current Protocols in Protein Science, John Wiley & Sons (1995)). For example, the frozen cells can be thawed, resuspended in buffer and ruptured by several passages through a small volume microfluidizer (Model M-1 105, Microfluidics International Corp., Newton, Mass.). The resultant homogenate is centrifuged to yield a clear supernatant (crude extract) and, following filtration, the crude extract is fractioned over columns. Fractions are monitored by absorbance at $OD_{280}$ nm and peak fractions may be analyzed by SDS-PAGE.

The concentrations of purified protein preparations are quantified 15 spectrophotometrically using absorbance coefficients calculated from amino acid content (Perkins, Eur. J. Biochem., 157:169-180 (1986)). Protein concentrations are also measured by the method of Bradford, Anal. Biochem., 72:248-254 (1976) and Lowry et al., J. Biol. Chem., 193:265-275 (1951) using bovine serum albumin as a standard.

SDS-polyacrylamide gels of various concentrations are purchased from BioRad (Hercules, Calif.), and stained with Coomassie blue. Molecular weight markers may include rabbit skeletal muscle myosin (200 kDa), E. coli-galactosidase (116 kDa), rabbit muscle phosphorylase B (97.4 kDa), bovine serum albumin (66.2 k.Da), ovalbumin (45 kDa), bovine carbonic anyhdrase (31 kDa), soybean trypsin inhibitor (21.5 kDa), egg white lysozyme (14.4 kDa) and bovine aprotinin (6.5 kDa). Proteins can also be isolated by other conventional means of protein biochemistry and purification to obtain a substantially pure product, i.e., 80, 95, or 99% free of cell component contaminants, as described in Jacoby, Methods in Enzymology, Vol. 104, Academic Press, New York (1984); Scoopes, Protein Purification, Principles and Practice, $2^{nd}$ Ed., Springer-Verlag, New York (1987); and Deutscher (ed.), Guide to Protein Purification, Methods in Enzymology, Vol. 182 (1990). If the protein is secreted, it can be isolated from the supernatant in which the host cell is grown; otherwise, it can be isolated from a lysate of the host cells.

Once a sufficient quantity of the desired protein has been obtained, it may be used for various purposes. One use of the protein or polypeptide is the production of antibodies specific for binding. These antibodies may be either polyclonal or monoclonal, and may be produced by in vitro or in vivo techniques well known in the art. Monoclonal antibodies to epitopes of any of the peptides identified and isolated as described can be prepared from murine hybridomas (Kohler, Nature, 25 6:495 (1975)). In summary, a mouse is inoculated with a few micrograms of protein over a period of two weeks. The mouse is then sacrificed. The cells that produce antibodies are then removed from the mouse's spleen. The spleen cells are then fused with polyethylene glycol with mouse myeloma cells. The successfully fused cells are diluted in a microtiter plate and growth of the culture is continued. The amount of antibody per well is measured by immunoassay methods such as ELISA (Engvali, Meth. Enzymol., 70:419 (1980)). Clones producing antibody can be expanded and further propagated to produce protein antibodies. Other suitable techniques involve in vitro exposure of lymphocytes to the antigenic polypeptides, or alternatively, to selection of libraries of antibodies in phage or similar vectors. See Huse et al., Science, 246:1275-128 1 (1989). For additional information on antibody production see Davis et al., Basic Methods in Molecular Biology, Elsevier, N.Y., Section 21-2 (1989). Such antibodies are particularly useful in diagnostic assays for detection of variant protein forms, or as an active ingredient in a pharmaceutical composition.

Example 1

Construction of Par-4 Deletion Mutants pCB6+ vector, pCB6+Par-4, pCB6+_Zip and 163 (Par-4DCTH) were described previously (Johnstone et al., (1996). pSV(gal was a gift from Brett Spear, University of Kentucky. The RelA luciferase reporter system composed of Gal4 luciferase (Gal4Luc) plasmid (that contains four Gal4 consensus DNA binding sites derived from the Saccharomyces cerevisiae located upstream of luciferase reporter gene), and Gal4RelA plasmid (containing the yeast Gal4 DNA binding domain fused to the transactivation domain (TA1) of RelA) were both from Dr. A. Baldwin (University of North Carolina at Chapel Hill, Chapel Hill, N.C.). The GFP cloning plasmids pcDNA3.1/CTGFPTOPO and pcDNA3.1/NTGFPTOPO were from Invitrogen Life Technologies, CA.

Par-4 (SEQ ID NO: 1) as a template, followed by ligation in pcDNA3.1/CTGFPTOPO and then left in the GFP plasmid or digested with XbaI and KpnI and subcloned into pCB6+.

Polyclonal antibodies for Par-4, NFkB (p65/RelA) and Fas were obtained from Santa Cruz Biotechnology, Inc., Calif. The anti-GFP rabbit polyclonal was from Torrey Pine Biolabs., CA. Terminal deoxynucleotide transferasemediated dUTPbiotin nick end labeling (TUNEL) enzyme and label were purchased from Roche Molecular Biochemicals, IN. The propidium iodide was from Clonetech, CA. and the Sepharose G protein was from Amersham Pharmacia Biotech., NJ.

Example 2

In vitro Activity of Par-4 Mutants on Cancer Cells

Androgen independent prostate cancer cells PC3 or DU145, androgen dependent prostate cancer cells LNCaP, normal primary prostatic cells PrE or PrS, NIH 3T3 fibroblast cells and NIH 3T3 Ras transformed fibroblast cells are known in the art. Androgen dependent prostate cancer cells LAPC4 were from Charles Sawyers (University of California at Los Angeles, Calif.) and MDA PCa 2b were from Nora Navone (M.D. Anderson Cancer Center, Tex.). Androgen independent prostate cancer cells LNCaP IGFBP5, which represent an isogenic derivative of LNCaP cells prepared by stable transfection with IGFBP5 expression construct, were provided by Martin Gleave (Vancouver General Hospital, British Columbia, Canada). Immortalized human prostate epithelial cells PZHPV7, and the head and neck cancer cells SQ20B and SCC66 were from Mansoor Ahmed, (University of Kentucky). The human lung cancer cells A549, H157, H838 and H460 were from John Yannelli (Internal Medicine Department, University of Kentucky). The human breast cancer cells MCF7 and MDA 231 were from GuoMin Li (Pathology, University of Kentucky). The immortalized breast epithelial cells MCF10a were from Johnson Lombardi (Georgetown University). Immortalized human endothelial cells HMEC were from Mariana Karakashian (University of Kentucky).

Cells were transiently transfected with the indicated plasmid constructs by using lipofectamine plus (from Invitrogen Life Technologies, CA) following the manufacturer's protocol. Cells were harvested after 48 hours, and whole cell lysates were subjected to Western blot analysis by using the Par-4 polyclonal antibody (from SantaCruz Biotechnology, Inc., CA), or luciferase and bgalactosidase assays as previously described) to quantify and normalize RelA activity. Cells were transfected with the appropriate plasmid construct. After fixing they were subjected to indirect immunofluorescence using secondary antibody conjugated with the fluorescent dye Alexa Fluor 488 (green) from Molecular Probes, Inc. For localization and apoptosis studies, nuclei were stained with propidium iodide (PI) or 4',6'-diamidino2phenylindole hydrochloride (DAPI) for 20 minutes after cell fixation.

Cells plated in chamber slides were transiently transfected with untagged or GFP tagged Par-4 or its derivatives. Apoptosis was determined by using TUNEL assay and DAPI staining. The cells expressing untagged protein were visualized by staining with antiPar-4 antibody followed by DAPI staining. Apoptotic nuclei were determined among transfected cells as described previously.

Figure 1B:
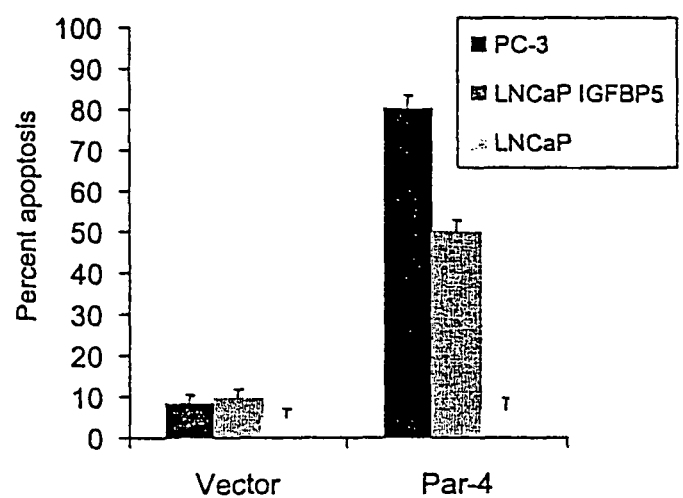

The results indicate that nuclear translocation of Par-4 correlates with susceptibility to apoptosis. Previous immunohistochemical studies localized Par-4 to both the cytoplasm and nucleus of prostate cells but exclusively to the cytoplasm of most tissues and nonprostatic cells. To determine the precise relationship between Par-4 localization and the induction of apoptosis, a broad panel of transformed and non-transformed cells was transiently transfected with GFPPar-4 or GFP vector for control, and the transfectants were studied for intracellular localization of Par-4 or apoptosis by confocal microscopy. These experiments included NIH 3T3 Ras, PC3 and DU145 that were previously shown to be sensitive apoptosis induction by Par-4; LNCaP, PrE, PrS and NIH 3T3 parental cells that were resistant to Par-4; and LNCaP IGFBP5 (an isogenic derivative of LNCaP), MDA MB2b, and LAPC4 that had not been previously tested. Representative examples of nuclear versus cytoplasmic expression and susceptibility to apoptosis are shown in FIG. 1 (A and B). It was noted that Par-4 nuclear presence correlated with its ability to induce apoptosis (See FIG. 1 and Table 1). Par-4 was detected in the nucleus and cytoplasm in androgen independent prostate cancer cells PC3, DU145, LNCaP derived cells LNCaP/IGFBP5, and Rastransformed NIH 3T3 cells. All of these cell lines were also sensitive to apoptosis induction by Par-4 (See Table 1, FIG. 1). However, Par-4 was strictly cytoplasmic in the apoptosis-resistant androgen dependent prostate cancer cells LNCaP, LAPC4 and MDA 2b, mouse immortalized fibroblast NIH 3T3 cells, and primary prostate epithelial cells PrE or primary prostate stromal cells PrS (See Table 1). Coexpression of dominant negative FADD or RelA, which inhibits Par-4 induced apoptosis, did not prevent Par-4 from translocation to the nucleus, suggesting that nuclear entry preceded apoptosis by Par-4.

It was discovered that NLS2, but not NLS1, is essential for nuclear entry. The 332 amino acid protein Par-4 has two putative nuclear localization sequences, NLS1 (amino acid 2025) and NLS2 (amino acid 137153) that are conserved in human, rat and mouse Par-4. To delineate the relationship between Par-4 entry into the nucleus and induction of apoptosis, Par-4 derivatives were prepared that lacked the NLS sequences (See FIG. 2A). PC3 cells were transiently transfected with these constructs and examined for nuclear entry, inhibition of NFkB transcription activity or apoptosis. Constructs DNLS1 showed nuclear entry, whereas DNLS2, which lacked an intact NLS2 domain, failed to translocate to the nucleus. This suggests that NLS2 is a functional nuclear localization sequence. Moreover, loss of DNLS2 but not DNLS1 abrogated the ability of Par-4 to inhibit NFkB transcription activity and induce apoptosis in PC3 cells (See FIG. 2B). These findings indicated that an intact NLS2 sequence was essential for nuclear entry of Par-4, and that the ability to inhibit NFkB transcription activity and to induce apoptosis correlated with nuclear entry of Par-4.

Figure 3A:
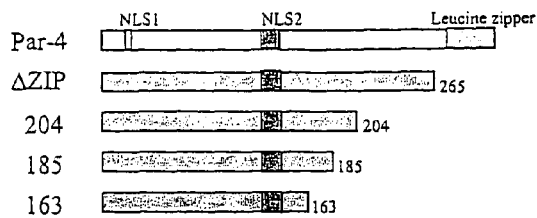
FIG. 3 shows that the leucine zipper domain is not essential for apoptosis. PC-3 cells were transiently transfected with untagged or GFP-tagged derivatives of various C-terminal deletion mutants of Par-4 (A). After 48 hours, the cells were examined for intracellular localization of the mutants (B), expression of the mutant proteins by Western blot analysis (C), inhibition of NF-B transcriptional activity (D), and apoptosis (E), as seen in FIG. 1. To examine Fas translocation (F), PC-3 cells were transiently transfected with untagged C-terminal deletion mutants, and after 48 hours they were stained with anti-Fas antibody. Alexa Fluor 488 green fluorescence was visualized by confocal microscopy.
Figure 3B:
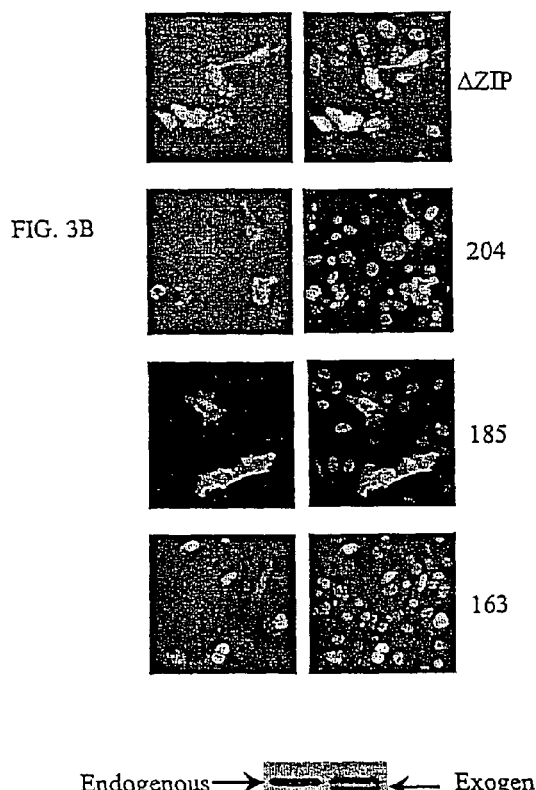
Figure 3C:
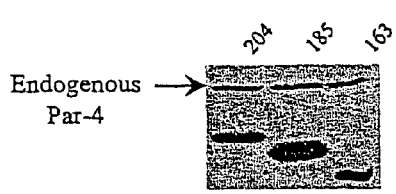
Figure 3D:
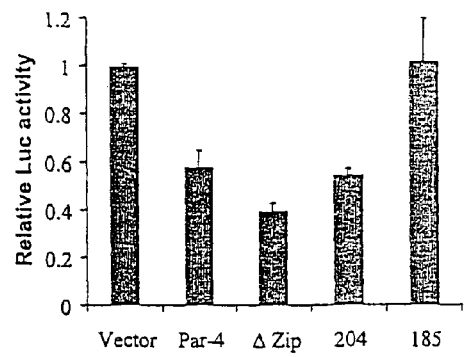
Figure 3D:
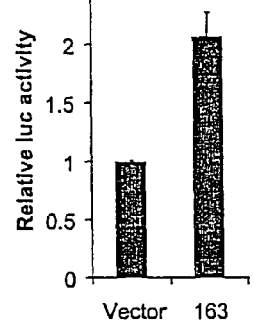
Figure 3E:
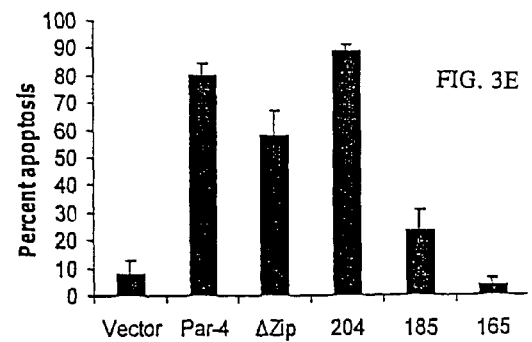
Figure 3F:
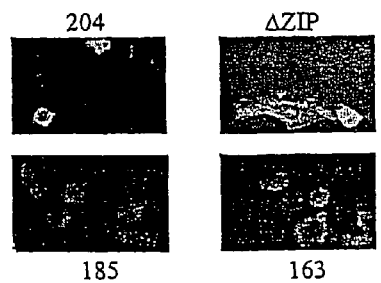

The leucine zipper domain of Par-4 is not essential for apoptosis. Other domains of Par-4 were sought which are essential for apoptosis. The C-terminal leucine zipper domain of Par-4 is required for sensitization of Par-4 resistant cells to apoptosis and for binding to all currently known partners of Par-4 including WT1, zPKC, p62 and Dlk. Transient transfection of a mutant lacking the leucine zipper domain (DZip) in PC3 cells resulted in direct induction of apoptosis (See FIG. 3E.) To further characterize the C-terminus of Par-4, various C-terminal deletion mutants were prepared and studied for nuclear localization, inhibition of NFkB transcription activity and apoptosis in PC3 cells. All C-terminal mutants of Par-4 had a tendency to translocate preferentially to the nucleus (See FIG. 3B), which suggests that the leucine zipper domain itself may prevent the nuclear translocation of the protein. As seen in FIGS. 3C and 3D), NFkB transcription activity and apoptosis were differentially affected by the extent of the C-terminal deletions. Par-4 mutants DZip and 1204 inhibited NFkB transcription activity and induced apoptosis. However, mutants 1185 and 1163 neither inhibited NFkB transcription activity nor did they induce apoptosis. Moreover, the ability to induce Fas trafficking to the cell membrane in these mutants correlated with their ability to induce apoptosis. These experiments indicated that the amino acids downstream of 204, including the leucine zipper domain, were dispensable for apoptosis by Par-4, and that binding to the partner proteins via the leucine zipper domain was not essential for apoptosis induction or inhibition of NFkB transcriptional activity by Par-4.

Example 3

Identification of the Core Domain of Par-4

Previously, NLS2 was identified as the most critical sequence for nuclear localization and apoptosis induction. To further confirm the importance of NLS2, two N-terminal deletion constructs 137332 were constructed and 148332 with either an intact NLS2 or a disrupted NLS2, respectively (See FIG. 4A). When PC3 cells were transfected with these constructs, 137332 but not 148332, was translocated to the nucleus (See FIG. 4B) and induced apoptosis. This suggested that NLS2 was critical for Par-4 function, and that the N-terminus of Par-4 was not required for Par-4 nuclear entry and apoptotic functions.

To define the minimal domain of Par-4 essential for apoptosis, additional constructs were made that began with the intact NLS2 domain at the amino terminus and with various deletions upstream of amino acid 204 (FIG. 4C). Transient transfection of PC3 cells indicated that 137195, but not 137190, inhibited NFkB transcription activity and induced apoptosis (See FIGS. 4D and 4E). Moreover, co-transfection of 137195 with dnFADD inhibited apoptosis (See FIG. 4G), indicating that similar to full length Par-4, the 137195 core domain induced apoptosis by activation of the Fas prodeath pathway together with inhibition of NFkB transcriptional activity. Thus, these findings identified 137195 as the minimal core domain of Par-4 that was essential and sufficient to induce apoptosis in PC3 cells.

Figure 5A:
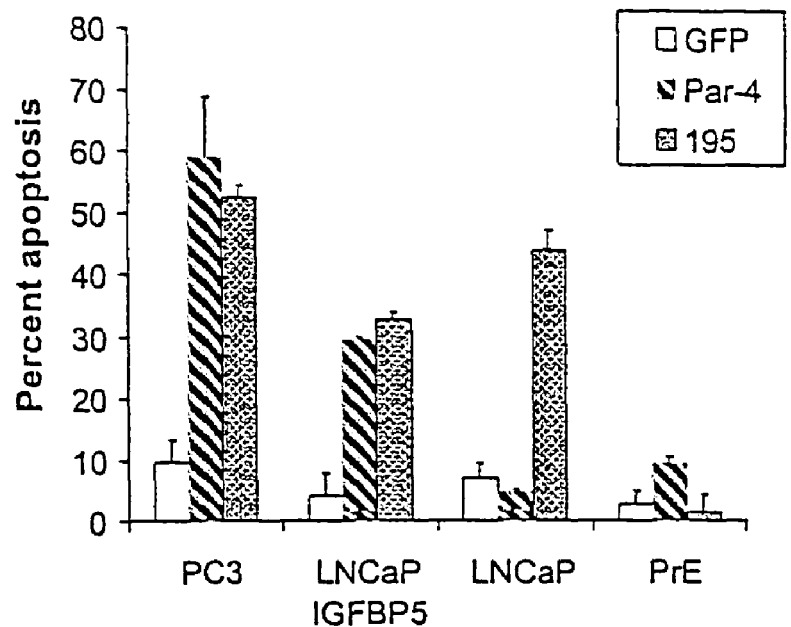
FIG. 5 shows that the core domain of Par-4 has an expanded but cancer-specific apoptotic ability. Various cell lines were transiently transfected with GFP vector, GFP-Par-4 or GFP-137-195, and examined for apoptosis in androgen-dependent or -independent prostate cancer cells or primary cells (A). LNCaP cells were transiently transfected with GFP vector or GFP-137-195, with or without dnFADD, and examined for apoptosis induction (B), as seen in FIG. 1.
Figure 5B:
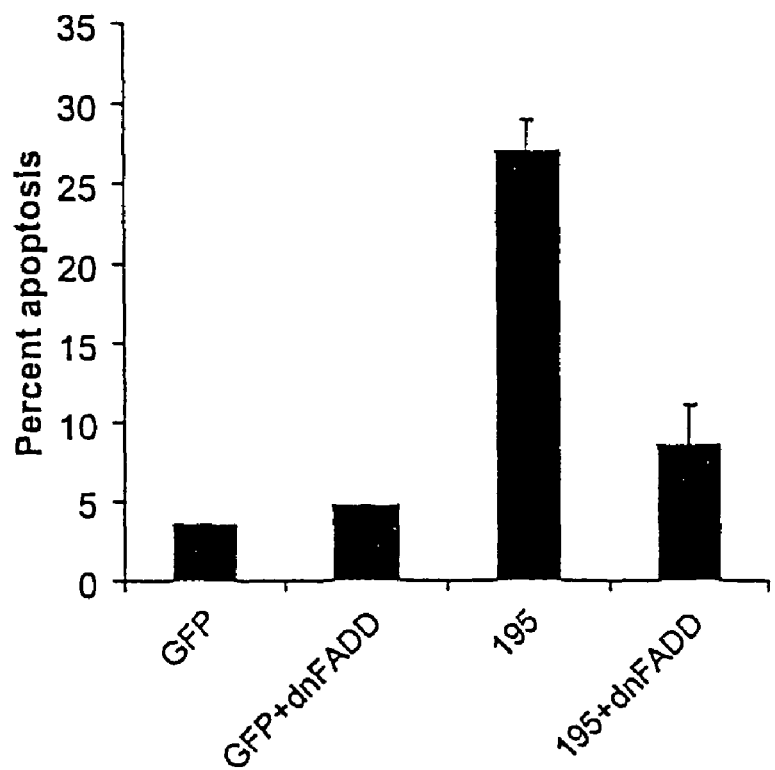

The core domain of Par-4 induces apoptosis specifically in cancer cells but not in normal cells. To determine whether similar to Par-4, the core domain 137195 induced apoptosis exclusively in androgen independent prostate cancer cells, a panel of androgen dependent or independent prostate cancer cells and primary normal cells were tested. 137195 induced apoptosis in both androgen independent and dependent prostate cancer cells but not in normal cells (See FIG. 5A). These data suggested the presence of an inhibitory domain in the C-terminus of Par-4 and that its deletion allowed 137195 to be functional in cells resistant to the apoptotic action of full length Par-4. In view of this expanded target range of 137195, the susceptibility of a broad panel of cancer and primary normal or immortalized cells to apoptosis by Par-4 or 137195 were studied, by using 137190 as a control. These experiments indicated that both Par-4 susceptible and Par-4 resistant cancer cells, regardless of whether or not they were of prostatic origin, were induced to undergo apoptosis by 137195 but not by 137190 (See Table 2). Neither Par-4 nor 137195 induced apoptosis in the primary normal or immortalized cells (See Table 2).

TABLE 1

Correlation between nuclear translocation and susceptible to apoptosis by Par-4.

| | Cells | Nuclear Par-4 | Cytoplasmic Par-4 | Apoptosis by Par-4 |
|---|---|---|---|---|
| androgen- | PC-3 | + | + | Sensitive[b] |
| | DU145 | + | − | Sensitive |
| | LNCaP | + | + | Sensitive |
| androgen- | LNCaP | − | + | Resistant[c] |
| | MDA MB2b | − | + | Resistant |
| | LAPC-4 | − | + | Resistant |
| immortalized | PZ-HPV-7 | − | + | Resistant |
| primary | PrE | − | + | Resistant |
| primary | PrS | − | + | Resistant |
| immortalized | NIH 3T3 | − | + | Resistant |
| transformed | NIH 3T3 | + | + | Sensitive |

[a]LNCaP IGFBP5 is an isogenic derivative of LNCaP cells.
[b]Sensitive: 50-75% of the transfected cells undergo apoptosis.
[c]Resistant: <10% of the transfected cells undergo apoptosis.

TABLE 2

137-195 mutant selectively kills cancer cells.

| | | | Apoptosis | Apoptosis | Apoptosis |
|---|---|---|---|---|---|
| Cancer Cells | Sensitive to | PC-3 | + | + | − |
| | | DU145 | + | + | − |
| | | LNCaP | + | + | − |
| | | MDA MB | − | + | − |
| | Resistant to | HMEC[d] | − | + | − |
| | | LNCaP | − | + | − |
| | | LAPC-4 | − | + | − |
| | | MDA 2b | − | + | − |
| | | MCF-7[f] | − | + | − |
| Immortalized | Resistant to | PA-HPV-7 | − | − | − |
| | | PrS | − | − | − |
| | | PrE | − | − | − |
| | | MCF10a[g] | − | − | − |

[a] + reflects apoptosis in 50-75% of the transfected cells.
[b] + reflects apoptosis in 25-35% of the transfected cells.
[c] − reflects apoptosis in <10% of the transfected cells for all the constructs regardless of the cancer or normal cell background.
[d]Human microvascular endothelial cells.
[e]estrogen-independent breast cancer cell line.
[f]estrogen-dependent breast cancer cell line.
[g]immortalized breast epithelial cell lines.

While this invention has been particularly shown and described with references to preferred embodiments thereof, it will be understood by those skilled in the art that various changes in form and details may be made therein without departing from the spirit and scope of the invention as defined by the appended claims.

All references discussed above are herein incorporated by reference in their entirety.

I claim:

1. An isolated rat prostate apoptosis responsive 4 (Par-4) protein fragment selected from the group consisting of amino acids 1-204, 137-221, 137-213, 137-198 and 137-195 of the Par-4 protein (SEQ ID NO: 1) wherein the Par-4 protein fragment is effective in reducing the size of tumors resistant to apoptosis by Par-4.

2. A method of producing a polypeptide, comprising incubating a host cell comprising a nucleic acid encoding the Par-4 protein fragment of claim 1 in operable linkage with a promoter under conditions that permit expression of the Par-4 protein fragment.

3. An isolated fusion polypeptide comprising a Par-4 fragment selected from the group consisting of amino acids 1-204, 137-221, 137-213, 137-198 and 137-195 of Par-4 protein (SEQ ID NO: 1).

4. A pharmaceutical composition for the treatment of cancer, comprising an isolated and purified Par-4 protein selected from the group consisting of amino acids 1-204, 137-221, 137-213, 137-198 and 137-195 of the Par-4 protein (SEQ ID NO: 1), and a pharmaceutically acceptable diluent, carrier or excipient.

* * * * *